United States Patent [19]

Szabo et al.

[11] Patent Number: 5,239,094
[45] Date of Patent: Aug. 24, 1993

[54] TETRAHYDRO-S-21-BR

[75] Inventors: Sandor Szabo, Brookline; John L. Neumeyer, Wayland; Philip LeQuesne, Newton Centre, all of Mass.

[73] Assignee: Brigham and Women's Hospital, Boston, Mass.

[21] Appl. No.: 683,956

[22] Filed: Apr. 12, 1991

[51] Int. Cl.$^5$ ............................................. C07J 7/00
[52] U.S. Cl. ................................... 552/592; 552/582
[58] Field of Search ........................ 552/588, 590, 592

[56] References Cited

U.S. PATENT DOCUMENTS 4,876,250 10/1989 Clark .................................... 514/179

OTHER PUBLICATIONS

Castellano, et al "The disordered structure of cortisol & iodocortisol" Acta Crystallogr., Sect B, B36(12), 3063–7 (1980) Chem Abstract 94:56328w.
Rapi, et al. "Amino- and Dienamino-derivatives formed from Adrenocortical Steroids and Heterocyclic Bases" JCS Perkin I, 502–507 (1972).
Cole, et al. "Conformational preference in the sidechain of compounds related to cortisone . . . " J. Chem. Soc. B, 4, 748–52 (1970).
Borrevang, Acta Chemica Scandinavica, 9, pp. 587–594 (1955).
Eng, et al. Journal of Labelled Compounds and Radiopharmaceuticals, vol XX, No. 1, pp. 63–72 (1983).
Folkman, et al. Science, vol. 235, pp. 442–447 (1987).
Crum et al., Science 230:1375 (1983).

Primary Examiner—Marianne M. Cintins
Assistant Examiner—Kimberly J. Kestler
Attorney, Agent, or Firm—Sterne, Kessler, Goldstein & Fox

[57] ABSTRACT

The invention is directed to novel angiotropic (angiogenic and angiostatic) steroids. They are halogenated in the 21 position. The invention is also directed to novel methods of treating gastrointestinal ulcers by the administration of the novel angiotropic (angiogenic) steroids.

1 Claim, No Drawings

TETRAHYDRO-S-21-BR

We described a new class of steroids which influence angiogenesis independently of their endocrine effects (*Science* 230:1375–78 (1985)). We have now tested the hypothesis that certain steroids might accelerate the healing of chronic duodenal ulcers and stimulate angiogenesis. S-D female rats (150–200g) were given cysteamine-HCl, 25 mg/100 g×3 by intragastric (i.g.) gavage on the first day and on the third day after laparotomy randomized into groups with vehicle solvent or steroids, mg/100 g i.g.×2/day. Autopsy was performed on day 21, ulcer craters measured and histologic sections taken. Control rats had chronic duodenal ulcers which measured (mean±SEM) $6.1\pm1.3$ mm$^2$ while after cortexolone (Reichstein substance S) or cortisone the ulcer craters (mm$^2$) were $3.1\pm0.8$ (not sign.=NS) or $0.9\pm0.8$ (p=0.001), respectively. Introduction of 21-bromide (Br) or iodide (I) usually improved the effect: ulcers after corticosterone, corticosterone-21-I or tetrahydro-S-21-Br (TSB) were $3.1\pm0.9$ (NS), $1.4\pm0.4$ (p=0.002), or $1.0\pm0.4$ (p=0.001), respectively. Only cortisone and corticosterone exerted mild glucocorticoid activity. In the chicken chorioallantoic membrane (CAM) assay for angiogenesis, TSB and cortisol-21-I exerted potent angiogenic activity, while cortisone-21-I (CI) was moderate and cortisone-21-Br mild. In the s.c. implanted sponge (5 mg of steroids) assays for the quantitative assessment of granulation tissue in a week, CI and TSB increased the area of granulation tissue by 151.4% and 353.6%, respectively, and TSB doubled the density of blood vessels. In fasted rats tetrahydro-S, TSB and cortexolone did not decrease gastric acid and pepsin secretion.

CONCLUSIONS

1. A new class of steroids enhanced the healing of cysteamine-induced chronic duodenal ulcers.
2. This effect is not associated with glucocorticoid or mineralocorticoid potency or inhibition of gastric secretion, and may be related to stimulation of granulation tissue production and angiogenesis
3. Angiotropic (angiogenic) steroids may represent a novel group of anti-ulcer agents.

What is claimed is:

1. An angiogenic steroid, wherein said steroid is tetrahydro-S-21-Br.

* * * * *